United States Patent
Wehling

(10) Patent No.: US 6,811,793 B2
(45) Date of Patent: Nov. 2, 2004

(54) EFFERVESCENT COMPOSITION INCLUDING STEVIA

(75) Inventor: Fred Wehling, Minneapolis, MN (US)

(73) Assignee: Amerilab Technologies, Inc., New Hope, MN (US)

( * ) Notice: Subject to any disclaimer, the term of this patent is extended or adjusted under 35 U.S.C. 154(b) by 163 days.

(21) Appl. No.: 10/096,417

(22) Filed: Mar. 11, 2002

(65) Prior Publication Data

US 2003/0170301 A1 Sep. 11, 2003

(51) Int. Cl.⁷ ............... A61K 9/46; A61K 9/20; A61K 9/00; A61K 33/00
(52) U.S. Cl. ............... 424/466; 424/464; 424/465; 424/43; 424/725; 514/960
(58) Field of Search ............... 424/400, 439, 424/441, 464, 465, 466, 43, 725, 484, 485, 488; 514/960, 961

(56) References Cited

U.S. PATENT DOCUMENTS

| | | | | |
|---|---|---|---|---|
| 4,082,858 | A | 4/1978 | Morita et al. | 426/597 |
| 4,127,645 | A | 11/1978 | Witzel et al. | 424/44 |
| 4,147,768 | A | 4/1979 | Shaffer et al. | 424/35 |
| 4,267,164 | A | 5/1981 | Yeh et al. | 424/44 |
| 4,552,771 | A | 11/1985 | Fülberth et al. | 426/548 |
| 4,599,403 | A | 7/1986 | Kumar | 536/18.1 |
| 5,112,610 | A | 5/1992 | Kienle | 424/195 |
| 5,171,571 | A | 12/1992 | Stephan et al. | 424/195 |
| 5,252,341 | A | 10/1993 | Sauerbier et al. | 424/489 |
| 5,516,529 | A | 5/1996 | Zellweger | 424/466 |
| 5,707,654 | A | 1/1998 | Béres et al. | 424/466 |
| 5,900,230 | A * | 5/1999 | Cutler | 424/49 |
| 5,925,378 | A * | 7/1999 | Carnazzo | 424/466 |
| 6,465,009 | B1 * | 10/2002 | Liu et al. | 424/464 |
| 6,524,626 | B2 * | 2/2003 | Chen | 424/728 |
| 6,589,555 | B2 * | 7/2003 | Pandya | 424/466 |

* cited by examiner

Primary Examiner—Michael G. Hartley
Assistant Examiner—Sharmila S. Gollamudi
(74) Attorney, Agent, or Firm—Allison Johnson, P.A.

(57) ABSTRACT

A tablet that includes stevia, water soluble binder, water soluble lubricant, active agent, and effervescent agent.

17 Claims, No Drawings

EFFERVESCENT COMPOSITION INCLUDING STEVIA

BACKGROUND OF THE INVENTION

The invention relates to formulating effervescent compositions that include stevia.

Effervescent compositions, when placed in water, evolve gas bubbles as they disintegrate. Effervescent compositions often exist in powder and tablet forms. Effervescent tablets are a useful dosage form for delivering active agents because they can be packaged in discreet and controlled quantities.

Effervescent tablets are often mass-produced using punch and die presses. The process of producing tablets, known as "tableting" or "compressing" requires the presence of a lubricant. The lubricant assists in reducing the friction that arises during the processes of compressing and ejecting the tablet. The absence of a lubricant can cause the tablet composition to stick to the punch face and the die wall of the tablet making apparatus, which can lead to irregular shaped tablets and a non-uniform distribution of ingredients within the tablet. These problems can be exacerbated in high speed tableting processes.

Lubricants can present difficulties when formulating effervescent compositions. Effervescent tablets preferably exhibit a fast rate of disintegration so that carbonate is present when the resulting composition is consumed and consumer preparation time inherent in the effervescent dosage form is minimized. Many lubricants retard the rate of disintegration.

In addition, consumers tend to prefer an effervescent tablet that dissolves in water to form a clear solution. Lubricants can cause "scumming" or agglomeration. Scumming refers to the presence of scum at the surface of the water in which the effervescent tablet has been dissolved. Scum is aesthetically undesirable and consumers tend to avoid using a dosage form that exhibits such a property. Stearates are one example of a class of water insoluble lubricants that tend to leave a scum on the surface of water.

Some consumers prefer compositions that include natural ingredients. Stevia is a natural extract found in the plant stevia rebaudiana and has sweetening properties. Other sweeteners such as aspartame, acesulfame potassium, cyclamate salts, and saccharin are synthetic.

SUMMARY

In one aspect, the invention features a tablet that includes stevia, water soluble binder, water soluble lubricant, active agent, and effervescent agent, the tablet exhibiting a hardness of at least 3 kp and being capable of disintegrating in water having a temperature of about 25° C. in less than 2.5 minutes. In one embodiment, the tablet exhibits a hardness of at least 6 kp. In another embodiment, the tablet disintegrates in no greater than 2 minutes in water having a temperature of about 25° C. In some embodiments, the tablet is essentially free of oil. In other embodiments, the tablet forms an essentially clear solution when disintegrated in water.

In one embodiment, the active agent is selected from the group consisting of water soluble active agents, substantially water dispersible active agents and combinations thereof. In some embodiments, the active agent includes vitamin, amino acid, pharmaceutical agent, mineral, dietary supplement or a combination thereof. In one embodiment, the active agent includes amino acid. In some embodiments, the active agent includes amino acid selected from the group consisting of L-tyrosine, isoleucine, ornithine, glutamine, phenylalanine, leucine, lysine, methionine, threonine, taurine, tryptophan, valine, alanine, glycine, arginine, histidine, cysteine, asparagine, proline, serine and mixtures thereof.

In one embodiment, the tablet further includes flavor agent, color agent, a sweetener, or a combination thereof.

In some embodiments, the effervescent agent includes an effervescent couple including acid and carbonate base. In other embodiments, the acid is selected from the group consisting of citric acid, tartaric acid, malic acid, fumaric acid, adipic acid, acid citrates, succinic acid and mixtures thereof. In another embodiment, the carbonate base is selected from the group consisting of sodium carbonate, potassium carbonate, sodium bicarbonate, potassium bicarbonate, calcium bicarbonate, magnesium carbonate, sodium glycocarbonate, carboxylysine and mixtures thereof.

In other embodiments, the water soluble lubricant includes polyethylene glycol. In some embodiments, the water soluble lubricant includes sodium benzoate. In one embodiment, the water insoluble lubricant includes from about 1% by weight to about 3% by weight sodium benzoate. In another embodiment, the composition is essentially free of water insoluble lubricant.

In one embodiment, the tablet includes from about 0.5% by weight to about 3% by weight stevia.

In other embodiments, the tablet includes stevia, water soluble binder, water soluble lubricant, active agent, and effervescent agent, the tablet, when disintegrated in water, forms an essentially scum free composition. In one embodiment, the tablet forms an essentially clear solution when dissolved in water.

In another embodiment, the tablet that includes stevia, water soluble binder, water soluble lubricant, active agent, effervescent agent, and no greater than 0.1% by weight water insoluble lubricant. In other embodiments, the tablet disintegrates in water having a temperature of about 25° C. in less than 2.5 minutes.

In some embodiments, the tablet includes stevia, polyethylene glycol, sodium benzoate, active agent, effervescent agent, and no greater than 1% by weight oil. In one embodiment, the tablet is essentially free of water insoluble lubricant. In another embodiment, the tablet is essentially free of oil. In other embodiment, the tablet disintegrates in less than 2.5 minutes in water at about 25° C. In some embodiments, the tablet disintegrates in less than 2 minutes in water at about 25° C.

In one embodiment, the tablet includes at least about 0.3% by weight stevia, from about 0.1% by weight to about 15% by weight polyethylene glycol and from about 0.1% by weight to about 15% by weight sodium benzoate. In some embodiments the tablet includes from about 0.5% by weight to about 3% by weight stevia, from about 1% by weight to about 5.5% by weight polyethylene glycol, and from about 1% by weight to about 3% by weight sodium benzoate.

In another aspect the invention features a tablet that includes stevia, water soluble binder, at least 3% by weight water soluble lubricant, active agent, and effervescent agent.

In other aspects the invention features a composition that includes stevia, water soluble binder, water soluble lubricant, and effervescent agent the composition forming an essentially scum free composition when disintegrated in water. In some embodiments, the composition dissolves in water to form an essentially clear solution. In other embodiments, the composition further includes active agent.

In one embodiment the composition includes stevia, water soluble binder, sodium benzoate, active agent, effervescent agent, and no greater than 1% by weight oil.

In other aspects, the invention features a method for treating a mammal that includes disintegrating an above described tablet or composition in liquid to form a composition, and administering the composition to the mammal. In some embodiments, the method for treating a mammal includes disintegrating an above-described tablet or composition in liquid to form a composition, and administering the composition to the mammal.

The effervescent composition provides an effervescent tablet that includes a natural sweetener. The effervescent tablet can be formulated to quickly dissolve in water to a clear solution that is free of an undesirable amount of scum. The effervescent tablet can also be formulated to exhibit a disintegration time of less than 2.5 minutes.

Other features of the invention will be apparent from the following description of preferred embodiments thereof, and from the claims.

DETAILED DESCRIPTION

The effervescent composition includes stevia, water soluble binder, lubricant, active agent and effervescent agent. The effervescent composition disperses in water, and preferably dissolves in water to form a clear solution essentially free of scum. The effervescent composition is preferably compressed into the form of a tablet that disintegrates in less than two and a half minutes, preferably in no greater than two minutes, when placed in room temperature (about 25° C.) water. Preferred effervescent tablets have a hardness of at least 3 kilopounds (Kp), preferably at least 6 Kp, more preferably from about 6 kp to about 10 kp, most preferably from about 6 kp to about 8 kp, as measured on a standard hardness tester fitted with a string gauge.

Stevia is a sweetener and can be found in nature in the plant stevia rebaudiana. Stevia is preferably present in the composition in an amount of at least 0.3% by weight, more preferably from about 0.4% by weight to about 6% by weight, most preferably from about 0.5% by weight to about 3% by weight.

The effervescent agent preferably is an effervescent couple that includes an acid and a base. The effervescent couple is activated when contacted with water, e.g., when the tablet is placed in a glass of water. The water liberates the acid and base and enables the acid and base to react with each other to produce carbon dioxide gas, which imparts carbonation to the aqueous composition. At least one component of the effervescent couple can also be an active agent. Examples of useful acids include citric acid, ascorbic acid, malic acid, adipic acid, tartaric acid, fumaric, succinic acid, sodium acid pyrophosophate, lactic acid, hexamic acid, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. Acid is present in the composition in an amount of from 10% by weight to about 60% by weight, more preferably from about 15% by weight to about 50% by weight, most preferably from about 25% by weight to about 40% by weight.

The base preferably is capable of generating carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide and mixtures thereof. The base is present in the composition in an amount of from 10% by weight to about 60% by weight, more preferably from about 15% by weight to about 50% by weight, most preferably from about 25% by weight to about 40% by weight.

The composition also includes binder. Examples of suitable binders include, e.g., starches, natural gums, cellulose gums, microcrystalline cellulose, methylcellulose, cellulose ethers, sodium carboxymethylcellulose, ethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof.

The composition includes a sufficient amount of binder to assist in holding the components of the composition together in the form of a tablet. Preferably binder is present in the composition in an amount of from 10% by weight to about 60% by weight, more preferably from about 15% by weight to about 50% by weight, most preferably from about 25% by weight to about 40% by weight.

Various lubricants are suitable for use in the composition including water dispersible, water soluble, water insoluble lubricants and combinations thereof. Preferred lubricants are water soluble. Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. Other water insoluble lubricants include, e.g., animal fats, polyoxyethylene monostearate, talc, sodium lauryl sulphate, magnesium oxide and combinations thereof.

The composition preferably includes a sufficient amount of lubricant to enable the composition to be formed into tablets and released from a high speed tableting press in the form of a tablet. The effervescent composition includes water soluble lubricant in an amount of from 1% by weight to about 15% by weight, preferably from about 1% by weight to about 12% by weight, more preferably from about 2% by weight to about 10% by weight, most preferably from about 3% by weight to about 8% by weight. Preferably the composition includes sodium benzoate in an amount of from 1% by weight to about 3% by weight and polyethylene glycol in an amount of from 1% by weight to about 5.5% by weight.

The composition preferably has less than 3% by weight water insoluble lubricants, more preferably less than 0.6% by weight water insoluble lubricants, most preferably no greater than 0.1% by weight water insoluble lubricants, and preferably no greater than 1% by weight oil, no greater than 0.5% by weight oil, more preferably no greater than 0.3% by weight oil, most preferably the composition is free of oil and other water insoluble lubricants.

Effervescent dosage forms are suitable for delivery of a variety of active agents including, e.g., vitamins, amino acids, pharmaceutical agents, minerals, dietary supplements, and combinations thereof. Suitable vitamins include, e.g., ascorbic acid (vitamin C), thiamin, riboflavin, nicotinic acid, pantothenic acid, pyridoxine, biotin, folic acid, vitamin B12, lipoic acid, ascorbic acid, vitamin A, vitamin D, vitamin E and vitamin K and coenzymes thereof, choline, carnitine, and alpha, beta, and gamma carotenes. Examples of coenzymes include thiamine pyrophosphates, flavin mononucleotide, flavin adenine dinucleotive, nicotinamide adenine dinucleotide, nicotinamide adenine dinucleotide phosphate coenzyme A pyridoxal phosphate, biocytin, tetrahydrofolic acid, coenzyme B12, lipoyllysine, 11-cis-retinal, and 1,25-dihydroxycholecalciferol and mixtures.

Suitable amino acids include, e.g., L-tyrosine, isoleucine, ornithine, glutamine, phenylalanine, leucine, lysine, methionine, threonine, taurine, tryptophan, valine, alanine, glycine, arginine, histidine, cysteine, asparagine, proline and serine, and mixtures thereof.

Suitable pharmaceutical agents include, e.g., antacids, analgesics, anti-inflammatories, antipyretics, antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers, peptides, proteins, oligonucleotides, and mixtures thereof.

Examples of minerals include calcium, iron, zinc, selenium, copper, iodine, magnesium, phosphorus, chromium and mixtures thereof.

Suitable dietary supplements include, e.g., bee pollen, bran, wheat germ, kelp, cod liver oil, ginseng, and fish oils, amino-acids, proteins, vitamins, minerals alpha-glycerylphosphorylcholine, acetyl-L-carnitine and salts thereof, docosahexaenoic acid, glucosamine, chondroitin, methylsulfonylmethane, and mixtures thereof.

The composition can also include other ingredients including, e.g., flavor agents, fillers, surfactants (e.g., polysorbate 80 and sodium lauryl sulfate), color agents including, e.g., dyes and pigments, and additional sweeteners.

Useful flavor agents include natural and synthetic flavoring sources including, e.g., volatile oils, synthetic flavor oils, flavoring aromatics, oils, liquids, oleoresins and extracts derived from plants, leaves, flowers, fruits, stems and combinations thereof. Useful flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Useful color agents include, e.g., food, drug and cosmetic (FD&C) colors including, e.g., dyes, lakes, and certain natural and derived colorants. Useful lakes include dyes absorbed on aluminum hydroxide and other suitable carriers.

Other sweetening agents can also be added to the effervescent composition. Examples of other sweeteners include sugars such as sucrose, glucose, invert sugar, fructose, and mixtures thereof, saccharin and its various salts (e.g., sodium and calcium salt of saccharin), cyclamic acid and its various salts, dipeptide sweeteners (e.g., aspartame), dihydrochalcone, glycyrrhizin, and sugar alcohols including, e.g., sorbitol, sorbitol syrup, mannitol and xylitol, and combinations thereof.

The effervescent composition is preferably stored in a moisture-proof package.

The invention will now be described by way of the following examples.

EXAMPLES

Examples E1–E4 and Controls C1–C4

Effervescent tablets were prepared by combining the ingredients in the amounts (reported in milligrams (mg)) set forth in Table 1 with mixing. The formulations were mixed for 20 minutes and then transferred to a tablet press having a one inch tool to form tablets weighing from approximately 3690 mg to 5120 mg. The tablets were pressed to a hardness of approximately four kilopounds.

The tablets were then placed in excess water, approximately 200 ml, and the amount of time required to achieve 100% disintegration was measured. The presence or absence of scum on the surface of the composition and the clarity of the composition were observed and noted. The results are reported in Table 1.

TABLE 1

| Compound | E1 | C1 | E2 | C2 | E3 | C3 | C4 | E4 |
| --- | --- | --- | --- | --- | --- | --- | --- | --- |
| Stevia | 30 | 30 | 30 | 30 | 30 | 36 | 30 | 30 |
| Aspartame | — | — | — | — | — | — | — | — |
| Mineral Oil | 10 | 25 | — | 25 | 10 | — | 35 | — |
| Cottonseed oil | — | — | — | ' | — | 25 | — | — |
| Magnesium Stearate | 10 | — | — | — | 10 | — | — | — |
| Sodium benzoate | — | — | 100 | — | — | — | — | 100 |
| PEG | 73.5 | 73.5 | 200 | 75 | 75 | — | — | 200 |
| Sorbitol | 735.9 | 735.9 | 585 | 585 | 585 | — | — | — |
| Sorbitol/mannitol blend | — | — | — | — | — | — | 950 | 950 |
| Lactose | — | — | — | — | — | 1000 | — | — |
| Ascorbic acid | 2157.1 | 2157.1 | 1075 | 1075 | — | — | — | — |
| L-Tyrosine | — | — | — | — | — | — | 1000 | 1000 |
| CaCO₃ | — | — | — | — | — | 1555 | — | — |
| Citric acid | 196.1 | 196.1 | 880 | 880 | 880 | 2300 | 1600 | 1600 |
| Sodium Bicarbonate | 833.4 | 833.4 | 830 | 830 | 830 | 100 | 540 | 540 |
| Potassium Bicarbonate | — | — | — | — | — | — | 360 | 360 |
| Soda Ash | 73.5 | 73.5 | 75 | 75 | 75 | — | — | — |

TABLE 1-continued

| Compound | E1 | C1 | E2 | C2 | E3 | C3 | C4 | E4 |
|---|---|---|---|---|---|---|---|---|
| Surfactant | — | — | — | — | — | 1 | 15 | 2 |
| * | 122.6 | 122.6 | 120 | 120 | 120 | 102.7[1] | 120.15 | 120.15 |
| Dissolution Time | 1 min 50 sec | 4 min | 1 min 45 sec | 3 min 30 sec | 1 min 45 sec | 4 min | 3 min 40 sec | 2 min |
| Visual Observations | Opaque liquid. Scum on top. | Opaque liquid. Some sediment on bottom | Clear liquid. No scum on top. No sediment on bottom. | Clear liquid. No sediment on bottom. | Clear liquid. Scum no top. | Milky white liquid. Some sediment on bottom. Scum on top. | Pink liquid. Foam on top. | Foam on top. Clear liquid. |

PEG = polyethylene glycol
* = flavor, color agent, caffeine or a combination thereof.
[1] = Includes 2.7 mg Vitamin D3

Other embodiments are within the claims.

What is claimed is:

1. A tablet comprising:
   at least about 0.3% by weight stevia;
   water soluble binder;
   from about 0.1% by weight to about 15% by weight polyethylene glycol;
   from about 0.1% by weight to about 15% by weight sodium benzoate;
   effervescent agent comprising acid and base; and
   no greater than 1% by weight oil.

2. The tablet of claim 1 comprising:
   from about 0.5% by weight to about 3% by weight stevia;
   from about 1% by weight to about 5.5% by weight polyethylene glycol; and
   from about 1% by weight to about 3% by weight sodium benzoate.

3. The tablet of claim 1 exhibiting a hardness of at least 6 kp.

4. The tablet of claim 1, wherein said tablet disintegrates in no greater than 2 minutes in water at a temperature of about 25° C.

5. The tablet of claim 1, wherein said tablet is essentially free of oil.

6. The tablet of claim 1, wherein said tablet forms an essentially clear solution when disintegrated in water.

7. The tablet of claim 1, wherein said active agent is selected from the group consisting of water soluble active agents, substantially water dispersible active agents and combinations thereof.

8. The tablet of claim 1, wherein said active agent comprises vitamin, amino acid, pharmaceutical agent, mineral, dietary supplement or a combination thereof.

9. The tablet of claim 1, wherein said active agent comprises ascorbic acid.

10. The tablet of claim 1, wherein said active agent comprises amino acid.

11. The tablet of claim 1, wherein said active agent comprises amino acid selected from the group consisting of L-tyrosine, isoleucine, ornithine, glutamine, phenylalanine, leucine, lysine, methionine, threonine, taurine, tryptophan, valine, alanine, glycine, arginine, histidine, cysteine, asparagine, proline, serine and mixtures thereof.

12. The tablet of claim 1 further comprising flavor agent, color agent, a sweetener, or a combination thereof.

13. The tablet of claim 1, wherein said acid is selected from the group consisting of ascorbic acid, citric acid, tartaric acid, malic acid, fumaric acid, adipic acid, acid citrates, succinic acid and mixtures thereof.

14. The tablet of claim 1, wherein said carbonate base is selected from the group consisting of sodium carbonate, potassium carbonate, sodium bicarbonate, potassium bicarbonate, calcium bicarbonate, magnesium carbonate, sodium glycocarbonate, carboxylysine and mixtures thereof.

15. The tablet of claim 1, wherein said tablet is essentially free of water insoluble lubricant.

16. The tablet of claim 1, wherein said tablet dissolves in water to form an essentially clear solution.

17. The tablet of claim 1, wherein said tablet disintegrates in water having a temperature of about 25° C. in less than 2.5 minutes.

* * * * *